(12) United States Patent
Desi Reddy et al.

(10) Patent No.: US 10,077,263 B2
(45) Date of Patent: Sep. 18, 2018

(54) PROCESS FOR THE PREPARATION OF APIXABAN

(71) Applicant: Optimus Drugs Private Limited, Hyderabad (IN)

(72) Inventors: Srinivas Reddy Desi Reddy, Hyderabad (IN); Dnyandev Ragho Rane, Hyderabad (IN); Venkata Srinivasa Rao Velivela, Hyderabad (IN)

(73) Assignee: Optimus Drugs Private Limited, Hyderabad (IN)

( * ) Notice: Subject to any disclaimer, the term of this patent is extended or adjusted under 35 U.S.C. 154(b) by 0 days.

(21) Appl. No.: 15/222,029

(22) Filed: Jul. 28, 2016

(65) Prior Publication Data
US 2017/0313695 A1   Nov. 2, 2017

(30) Foreign Application Priority Data

Apr. 29, 2016  (IN) .......................... 201641014966A

(51) Int. Cl.
*C07D 471/04* (2006.01)
*C07D 413/14* (2006.01)

(52) U.S. Cl.
CPC ......... *C07D 471/04* (2013.01); *C07D 413/14* (2013.01)

(58) Field of Classification Search
CPC ........................... C07D 471/04; C07D 413/14
See application file for complete search history.

(56) References Cited

U.S. PATENT DOCUMENTS 6,413,980 B1   7/2002  Fevig et al.
6,967,208 B2   11/2005  Pinto et al.

FOREIGN PATENT DOCUMENTS

WO   WO 2003/049681 A2   6/2003

*Primary Examiner* — Rebecca L Anderson
(74) *Attorney, Agent, or Firm* — Ladas & Parry LLP

(57) ABSTRACT

The present invention relates to an improved process for the preparation of Apixaban and its intermediates.

2 Claims, No Drawings

PROCESS FOR THE PREPARATION OF APIXABAN

FIELD OF THE INVENTION

The present invention relates to an improved process for the preparation of Apixaban and its intermediates.

BACKGROUND OF THE INVENTION

Apixaban (INN, trade name Eliquis) is a selective inhibitor of FXa and it is approved by the USFDA for the prevention of venous thromboembolic events (VTE) in adults, who have undergone elective hip or knee replacement surgery.

Apixaban is chemically known as 1-(4-methoxyphenyl)-7-oxo-6-[4-(2-oxopiperidin-1-yl)phenyl]-4,5,6,7-tetra-hydro-1H-pyrazolo[3,4c]pyridine-3-carboxamide of formula I. The empirical molecular formula is $C_{25}H_{25}N_5O_4$. Its molecular weight is 459.5, and its chemical structure is represented below:

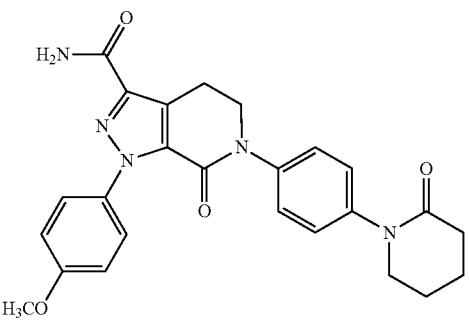

Apixaban was first generically disclosed in U.S. Pat. No. 6,413,980 and later it has been specifically disclosed in U.S. Pat. No. 6,967,208. The process for its preparation comprises reacting 4-iodo aniline (VIII) with 5-bromo valeryl chloride to form the compound of formula (VII). The compound of formula (VII) is treated with phosphorous pentachloride and excess morpholine to provide compound of formula (VI), further it is reacted with the compound of formula (V), followed by δ-valerolactam in an Ullmann condensation to get the compound of formula (II). The amidation has been taken place in presence of ethylene glycol and aqueous ammonia to afford the compound of formula (I).

The above synthetic process is illustrated as per the following Scheme-I

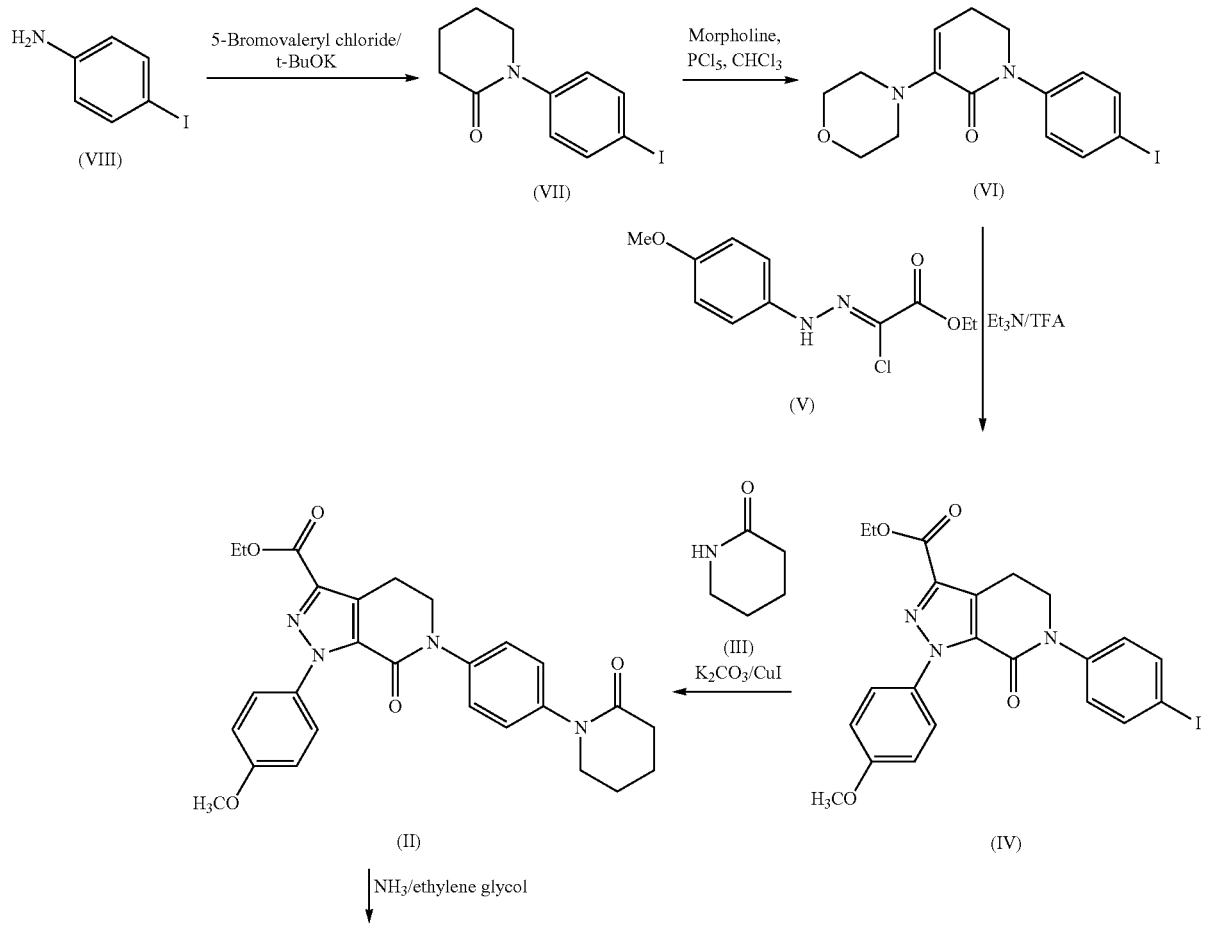

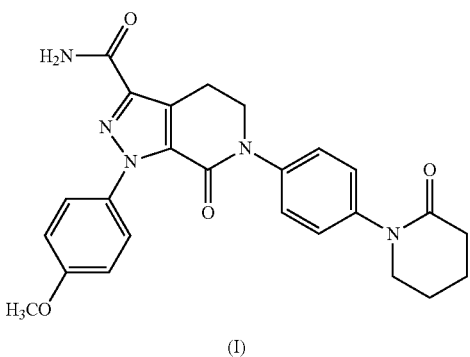

(I)

WO 2003/049681 discloses a process for the preparation of Apixaban by two synthetic routes. The first synthetic route comprises a reaction of δ-valerolactam (III) with phosphorus pentachloride to provide the compound of formula (IX), which is further reacted with lithium carbonate in DMF followed by morpholine in the presence of triethylamine to produce the compound of formula XI. The compound of formula XI is condensed with the compound of formula (V) to give the compound of formula (XII). The condensation of the compounds of formulas (XII) and (VII) in the presence of potassium carbonate and cuprous iodide as catalyst yields the compound of formula (II), followed by reaction with isobutylchloroformate to form a mixed acid anhydride, which is then transferred with excess ammonia solution to the compound of formula (I).

The above described synthetic process is illustrated as per following Scheme-II

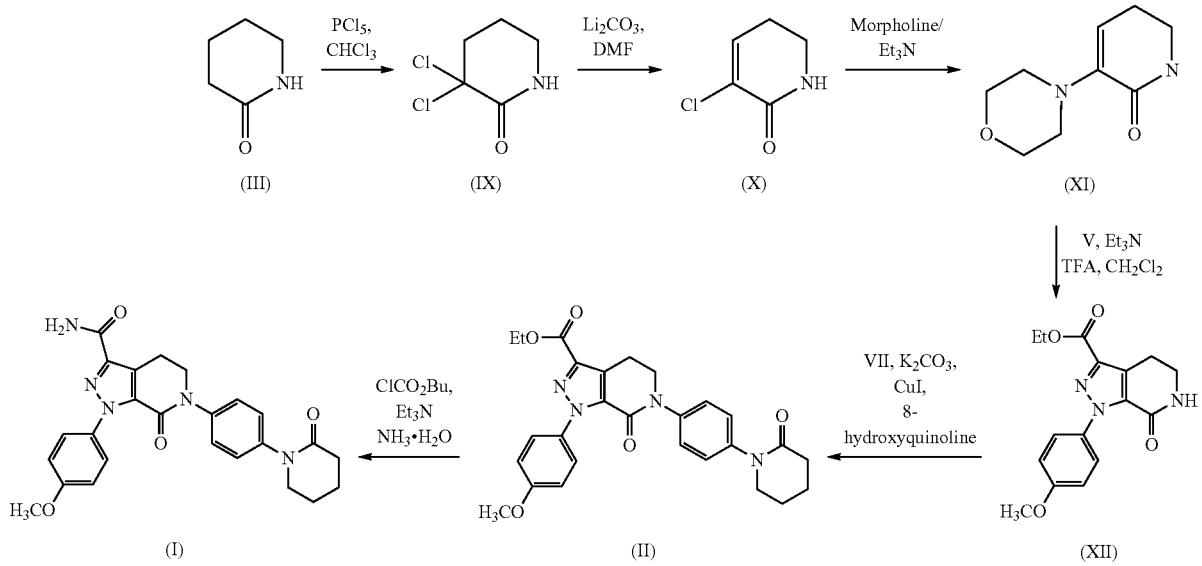

In the second synthetic route disclosed in WO '681, the compound of formula (XIII) is reacted with morpholinein excess to give the compound of formula (VI), which is further treated with δ-valerolactam (III) in the presence of $Cs_2CO_3$ and $Cu(PPh_3)_3Br$ to give the compound of formula (XIV). The compound of formula (XIV) is condensed with the compound of formula (V) to give a compound of formula (II) and followed by the addition of an excess of sodium methoxide and 10 equivalents of formamide to obtain the compound of formula (I).

The above described synthetic process is illustrated as per following Scheme-III

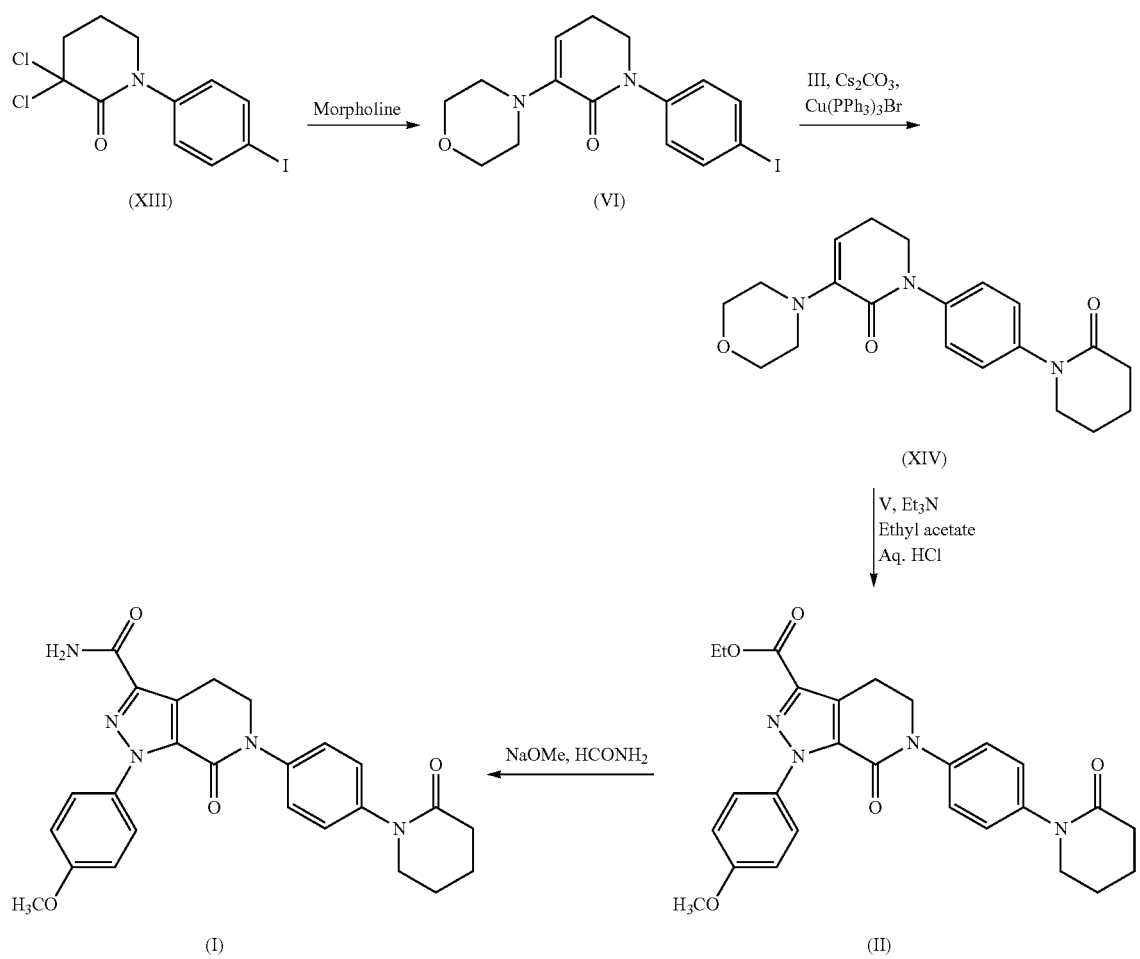

Scheme-III

The complex processes for the preparation of the Apixaban and its intermediates, which are known from the prior art, comprise the use of expensive and corrosive/toxic reagents and require drastic reaction conditions. The above-mentioned reagents and process conditions—especially those required for preparing the Apixaban intermediate, 3-morpholine-4-yl-1-[4-(2-oxo-piperidin-1-yl)phenyl]-5,6-dihydro-1H-pyridin-2-one of formula (XIV)—are difficult to handle and to apply in industrially scale.

Hence, there is consequently a need for an improved method for the preparation of Apixaban and its intermediates which does not involve the problems described above. Said method particularly should result in less impurities, should be industrially scalable, should allow the desired compounds to be obtained with high yields, should use cheaper reagents which are simpler to handle and eco-friendly, and should also use mild reaction conditions.

The inventors of the present invention have developed an improved process for preparing Apixaban being more eco-friendly as well as cost-effective and providing good yields and an improved purity.

SUMMARY OF THE INVENTION

One aspect of the present invention is to provide an improved process for the preparation of 3-morpholine-4-yl-1-[4-(2-oxo-piperidin-1yl)phenyl]-5,6-dihydro-1H-pyridin-2-one (XIV) comprising the steps of;

a) reacting 4-iodoaniline (VIII) with 5-bromo valeryl chloride in the presence of an organic base to produce 5-bromo pentanoic acid (4-iodophenyl)amide (XV), b) treating the product of step-a) with an inorganic base in the presence of a suitable organic solvent to produce 1-(4-iodo-phenyl)-piperidin-2-one (VII), c) reacting the product of step-b) with phosphorous pentachloride in the presence of a suitable organic solvent to produce 3,3-dichloro-1-(4-iodo-phenyl)-piperidin-2-one (XIII), d) reacting the product of step-c) with morpholine 1-(4-iodo-phenyl)-3-morpholin-4-yl-5,6-dihydro-1H-pyridin-2-one (VI), e) condensing the product of step-d) with 6-valerolactam in the presence of an inorganic base/catalyst and, f) isolating 3-morpholine-4-yl-1-[4-(2-oxo-piperidin-1 yl)phenyl]-5,6-dihydro-1H-pyridin-2-one (XIV).

The above synthetic process is illustrated as per the following Scheme-IV

Scheme-IV

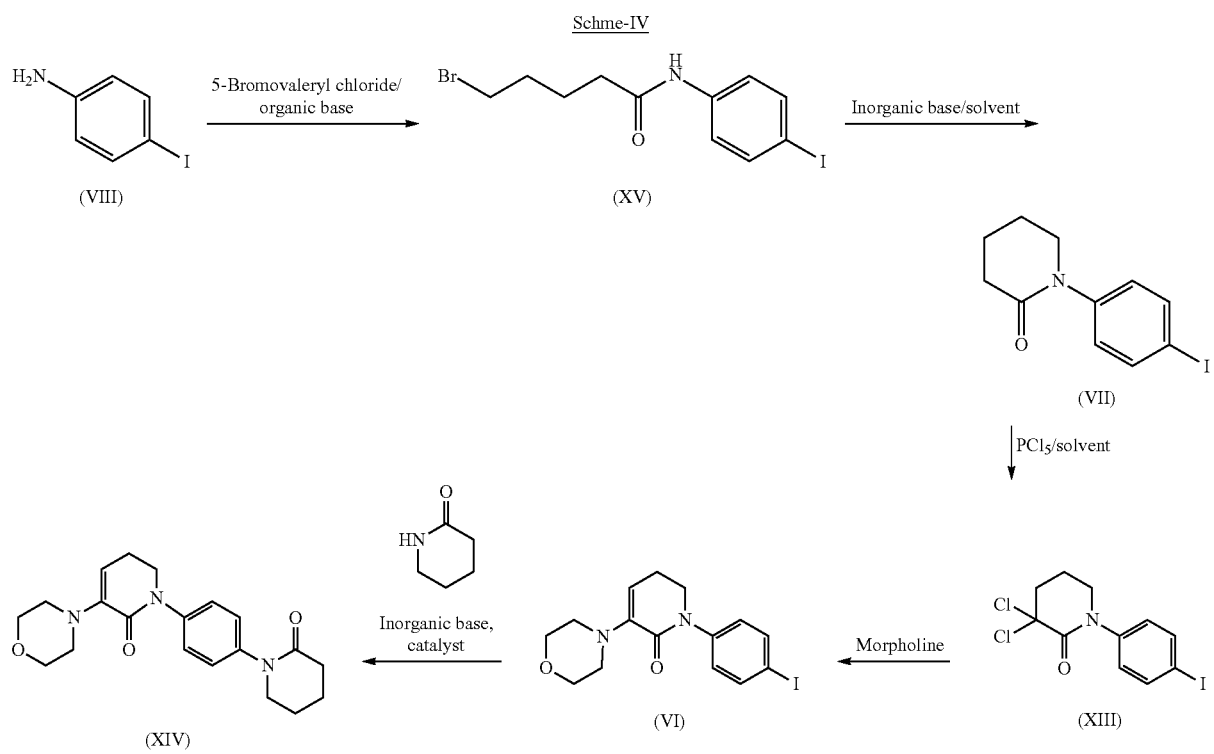

Another aspect of the present invention is to provide an improved process for the preparation of Apixaban of formula I comprising the steps of;
a) condensing morpholine 1-(4-iodo-phenyl)-3-morpholin-4-yl-5,6-dihydro-1H-pyridin-2-one (VI) with δ-valerolactam in the presence of an inorganic base and catalyst to produce 3-morpholine-4-yl-1-[4-(2-oxo-piperidin-1yl)phenyl]-5,6-dihydro-1H-pyridin-2-one (XIV),
b) reacting the product of step-a) with ethyl (2Z)-chloro [2-(4-methoxyphenyl) hydrazinylidene]ethanoate (V) in the presence of a suitable organic solvent and a base, followed by a treatment with an acid to produce 1-(4-methoxy-phenyl)-7a-morpholin-4-yl-7-oxo-6-[4-(2-oxo-piperidin-1-yl)-phenyl-3a,4,5,6,7,7a-hexahydro-1H-pyrazolo[3,4-c]pyridine-3-carboxylic acid ethyl ester (II),
c) amidation the product of step-b), and
d) isolating Apixaban of formula I.

The above synthetic process is illustrated as per the following Scheme-V

Scheme-V

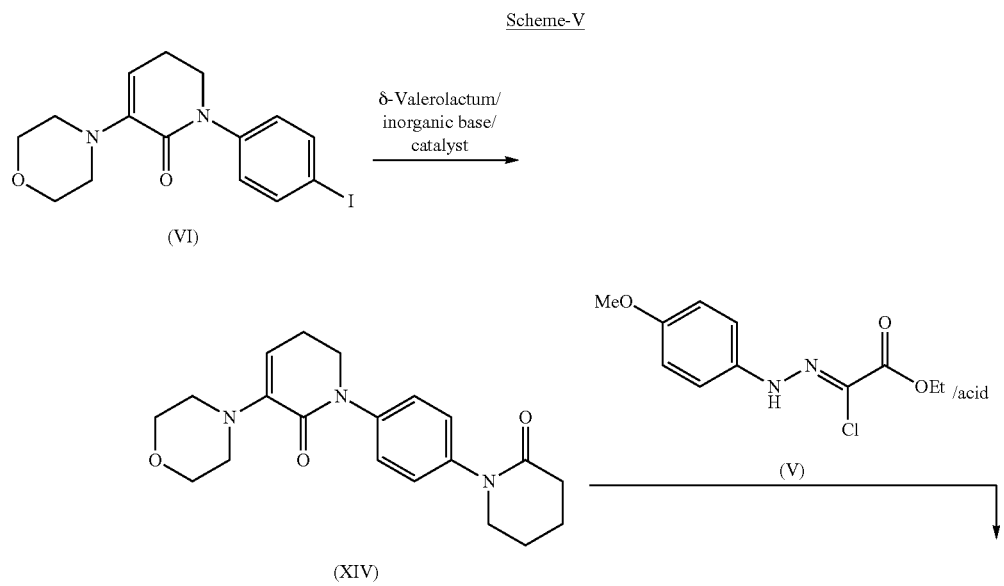

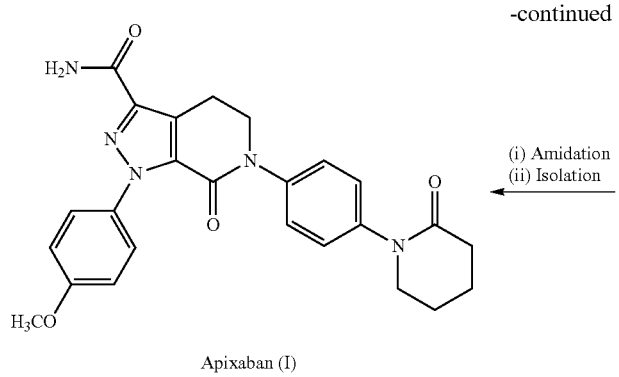

Apixaban (I)

(i) Amidation
(ii) Isolation

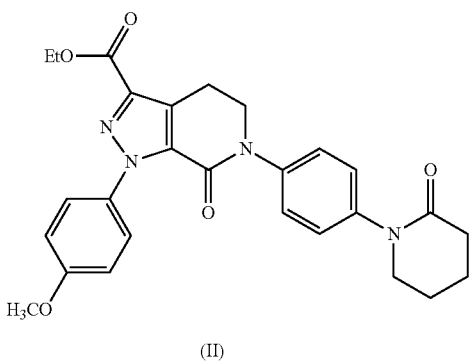

(II)

DETAILED DESCRIPTION OF THE INVENTION

The present invention provides an improved, cost-effective, and eco friendly process for the preparation of Apixaban in good yields.

In one embodiment, the present invention relates to a process for the preparation of 3-morpholine-4-yl-1-[4-(2-oxo-piperidin-1yl)phenyl]-5,6-dihydro-1H-pyridin-2-one of formula (XIV), which comprises the steps of
 a) reacting 4-iodoaniline (VIII) with 5-bromo valeryl chloride in the presence of an organic base to produce 5-bromo pentanoic acid (4-iodophenyl)amide (XV),
 b) treating the product of step-a) with an inorganic base in the presence of a suitable organic solvent to produce 1-(4-iodo-phenyl)-piperidin-2-one (VII),
 c) reacting the product of step-b) with phosphorous pentachloride in the presence of an organic solvent to produce 3,3-dichloro-1-(4-iodo-phenyl)-piperidin-2-one (XIII),
 d) reacting the product of step-c) with morpholine 1-(4-iodo-phenyl)-3-morpholin-4-yl-5,6-dihydro-1H-pyridin-2-one (VI),
 e) condensing the product of step-d) with δ-valerolactam in the presence of an inorganic base/catalyst and,
 f) isolating 3-morpholine-4-yl-1-[4-(2-oxo-piperidin-1yl) phenyl]-5,6-dihydro-1H-pyridin-2-one (XIV).

An aspect of the present invention is the provision of a process for preparing the compound of formula (XIV) comprising the reaction of 4-iodoaniline with bromo valeryl chloride in the presence of an organic base and a suitable organic solvent at a temperature of below 5° C. to 15° C. to provide the compound of formula (XV) as an intermediate.

Further, the compound of formula (XV) is treated with an inorganic base in the presence of a suitable organic solvent at a temperature of 25° C. to 35° C. and heated to reflux (e.g., at 100° C. to 120° C.). After completion of the reaction, the mixture is allowed to cool to produce the compound of formula (VII).

The compound of formula (VII) is reacted with phosphorous pentachloride in the presence of a suitable organic solvent. The reaction mixture is heated to reflux (e.g., at 100° C. to 120° C.) and allowed to cool to room temperature to give a compound of formula (XIII).

The compound of formula (XIII) is allowed to react with morpholine at a temperature of 25° C. to 35° C. and heated to reflux for completing the reaction yielding the compound of formula (VI).

The obtained compound of formula (VI) is reacted with δ-valerolactam in the presence of an inorganic base and a catalyst to provide the compound of formula (XIV).

According to a specific embodiment of the invention, the organic base used in reaction step-a) is selected from dimethylaminopyridine (DMAP), 5-ethyl-2-methyl pyridine, pyridine, diisopropyl ethylamine, diethylamine, triethylamine, N-methyl pyrrolidone, piperidine, and mixtures thereof; preferably dimethylaminopyridine and triethylamine.

According to a further specific embodiment of the invention, the inorganic base used in reaction step-e) is selected from tripotassium phosphate ($K_3PO_4$), sodium carbonate and potassium bicarbonate, preferably tripotassium phosphate.

According to a further specific embodiment of the invention, the catalyst used in reaction step-e) is selected from $Cu(PPh_3)_3Br$, CuBr, CuI, and quatenary ammonium salts such as benzyltrimethylammonium chloride, diallyldimethylammonium chloride, benzyltrimethylammonium bromide, n-octyltrimethylammonium bromide, stearyltrimethylammonium bromide, cetyldimethylammonium bromide, tertiary butyl ammonium bromide, tetra n-butylammonium iodide, β-methylcholinium iodide, tetra n-butylammonium hydrogensulfate, phenyltrimethylammonium hydroxide, etc.

According to a further specific embodiment of the invention, the suitable organic solvent in all steps is (independently) selected from the group of methylene dichloride, chloroform, ethyl acetate, toluene, xylene, methanol, ethanol, isopropanol, dimethyl formamide, dimethyl sulfoxide, tetrahydrofuran, or methyl ethyl ether.

Another aspect of the present invention is to provide an improved process for the preparation of Apixaban of formula (I) comprising the steps of
 a) condensing morpholine 1-(4-iodo-phenyl)-3-morpholin-4-yl-5,6-dihydro-1H-pyridin-2-one (VI) with δ-valerolactam in the presence of an inorganic base and a catalyst to produce 3-morpholine-4-yl-1-[4-(2-oxo-piperidin-1yl) phenyl]-5,6-dihydro-1H-pyridin-2-one (XIV),
 b) reacting the product of step-a) with ethyl (2Z)-chloro [2-(4-methoxyphenyl) hydrazinylidene] ethanoate (V) in the presence of a solvent and a base, followed by a treatment with an acid to produce 1-(4-methoxy-phenyl)-7a-morpholin-4-yl-7-oxo-6-[4-(2-oxo-piperidin-1-yl) phenyl-3a,4,5,6,7,7a-hexahydro-1H-pyrazolo[3,4-c]pyridine-3-carboxylic acid ethyl ester (II),
 c) amidation the product of step-b), and
 d) isolating the Apixaban of formula I.

A further aspect of the present invention is to provide a process for the preparation of Apixaban by reacting the compound of formula (VI). Further, the compound of formula (VI) is reacted with the compound of formula (V) in the presence of a suitable organic solvent and the reaction mixture is heated to reflux until completion of the reaction. After completion of reaction, water is added, the organic layer is separated, and the solvent is distilled off to get a residue. The residue is treated with an acid to give a compound of formula (II); followed by the addition of an excess of sodium methoxide and 5 to 10 equivalents of formamide to obtain Apixaban of formula (I).

According to a specific embodiment of the present invention, the inorganic base in reaction step-a) is selected from tripotassium phosphate ($K_3PO_4$), sodium carbonate, and potassium bicarbonate.

According to a further specific embodiment of the present invention, the catalyst used in reaction step-e) is selected from $Cu(PPh_3)_3Br$, CuBr, CuI and quatenary ammonium salts such as benzyltrimethylammonium chloride, diallyldimethylammonium chloride, benzyltrimethylammonium bromide, n-octyltrimethylammonium bromide, stearyltrimethylammonium bromide, cetyldimethylammonium bromide, tertiary butyl ammonium bromide, tetra n-butylammonium iodide, p-methylcholinium iodide, tetra n-butylammonium hydrogensulfate, phenyltrimethylammonium hydroxide, etc.

According to a further specific embodiment of the present invention, the acid in reaction step-c) is selected from hydrochloride acid and trifluoro acetic acid.

According to a further specific embodiment of the present invention, the suitable organic solvent in all steps is (independently) selected from the group of methylene dichloride, chloroform, ethyl acetate, toluene, xylene, methanol, ethanol, isopropanol, dimethyl formamide, dimethyl sulfoxide, tetrahydrofuran, or methyl ethyl ether.

According to a further specific embodiment of the present invention, the obtained compound of formula (I) or apixaban has HPLC purity of not less than 99%.

The process details of the invention are provided in the examples given below, which are provided by way of illustration only and therefore should not be construed to limit the scope of the invention.

Example-1

Preparation of 5-bromo-pentanoic acid (4-iodo-phenyl)-amide

Method-A:
4-Iodoaniline (400 g, 1.826 moles), triethylamine (258 g, 2.557 moles) and dimethylamino pyridine (10 g) were dissolved in ethyl acetate (2000 ml) and cooled to 5 to 15° C. 5-Bromovaleryl chloride (474 g, 2.374 moles) dissolved in ethyl acetate (100 ml) was added dropwise to the reaction mixture over a period of 2.5-3 hrs at the same temperature. After completion of the reaction, the obtained solid was filtered, washed with water (1000 ml) and dried to get 530 g (76%) of the title compound.
Method-B:
4-Iodoaniline (40 g, 0.18 moles), triethylamine (25.8 g, 0.25 moles) and dimethylamino pyridine (1 g) were dissolved in methylene dichloride (200 ml) and cooled to 5 to 15° C. 5-Bromovaleryl chloride (47.4 g, 0.237 moles) dissolved in methylene dichloride (20 ml) was added dropwise to the reaction mixture over a period of 2.5-3 hrs at the same temperature. After completion of the reaction, the obtained solid was filtered, washed with water (100 ml) and dried to get 52 g (74%) of the title compound.

Method-C:
4-Iodoaniline (40 g, 0.18 moles), triethylamine (25.8 g, 0.25 moles) and dimethylamino pyridine (1 g) were dissolved in toluene (200 ml) and cooled to 5 to 15° C. 5-Bromovaleryl chloride (47.4 g, 0.237 moles) dissolved in toluene (20 ml) was added dropwise to the reaction mixture over a period of 2.5-3 hrs at the same temperature. After completion of the reaction, the obtained solid was filtered, washed with water (100 ml) and dried to get 50 g (71%) of the title compound.

Example-2

Preparation of 1-(4-iodo-phenyl)-piperidin-2-one

Method-A:
5-Bromo-pentanoic acid (4-iodo-phenyl)-amide (500 g, 1.305 moles), tripotassium phosphate (691 g, 3.263 moles), and dimethyl formamide (500 ml) were dissolved in toluene (2000 ml) at ambient temperature. The reaction mass was heated to reflux at about 110° C. and maintained at that temperature for 7 hrs. After completion, the reaction mixture was cooled to room temperature and water (5000 ml) was added to obtain separate layers. The isolated toluene layer was distilled off under vacuum at below 70° C. The obtained reaction mass was cooled to room temperature, followed by the addition of n-hexane (500 ml). The resulting mixture was stirred. The resultant solid was filtered off and dried to get the title compound 340 g (79%).
Method-B:
5-Bromo-pentanoic acid (4-iodo-phenyl)-amide (50 g, 0.1305 moles) and tripotassium phosphate (69.1 g, 0.326 moles) were dissolved in toluene (200 ml) at ambient temperature. The reaction mass was heated to reflux at about 110° C. and maintained at that temperature for 24-26 hrs. After completion, the reaction mixture was cooled to room temperature and water (500 ml) was added to obtain separate layers. The isolated toluene layer was distilled off under vacuum at below 70° C. The obtained reaction mass was cooled to room temperature, followed by the addition of n-hexane (50 ml). The resulting mixture was stirred. The resultant solid was filtered off and dried to get the title compound 30 g (70%).

Example-3

Preparation of 3,3-dichloro-1-(4-iodo-phenyl)-piperidin-2-one

To a solution of 1-(4-iodo-phenyl)-piperidin-2-one (350 g, 1.158 moles) in methylene dichloride (3500 ml) phosphorous pentachloride (724 g) was added over a period of 1 hr. After completion of the addition, the reaction mixture was refluxed for 2-3 hrs. The reaction mixture was quenched in crushed ice (5000 ml) at 0-5° C. over a period of 1 hr and stirred to obtain separate layers. The organic layer was isolated and the solvent was distilled off under reduced pressure to get a residue, which it was cooled and recrystallized from isopropanol.

The resultant solid was filtered and dried to obtain 300 g (82%) of the title compound.

Example-4

Preparation of 1-(4-Iodo-phenyl)-3-morpholin-4-yl-5,6-dihydro-1H-pyridin-2-one 3,3-Dichloro-1-(4-iodo-phenyl)-piperidin-2-one (300 g, 0.810 moles) and morpholine (300 ml) were suspended in dimethyl formamide (600 ml) at ambient temperature. The reaction mixture was heated to 105-110° C. for 5-6 hrs. After completion, the reaction mixture was cooled to room temperature; followed by the addition of toluene (1500 ml) and water (3000 ml) and stirred to separate layers. The toluene layer was isolated and the solvent was evaporated under reduced pressure at below 70° C. The solid was cooled and recrystallized from n-hexane (600 ml). The resultant solid was filtered and dried to obtain 273 g (87%) of the title compound.

Example-5

Preparation of 3-morpholin-4-yl-1-[4-(2-oxo-piperidin-1-yl)-phenyl]-5,6-dihydro-1H-pyridin-2-one A suspension of 1-(4-iodo-phenyl)-3-morpholin-4-yl-5,6-dihydro-1H-pyridin-2-one (75 g, 0.194 moles), 2-piperidone (48 g, 0.485 moles) and tripotassium phosphate (103 g, 0.485 moles) in xylene (750 ml) was treated with Cu(PPh$_3$)$_3$Br (54.5 g, 0.058 moles) at room temperature and heated to reflux by using a dean stark water separator for 8-10 hrs. After completion, the reaction mass was cooled to 0-5° C. Aqueous ammonia (750 ml) and ethyl acetate (1125 ml) were added to the reaction mixture and stirred for 2-3 hrs. The resultant solid was filtered and washed with ethyl acetate (20 ml) to get a solid, which was dissolved in methylene dichloride (375 ml) at 35-40° C. and treated with activated carbon. The resultant solution was filtered through a hyflow bed and distilled under vacuum to get an residue; followed by addition of methanol (90 ml) and the reaction mass was cooled to 0-5° C., stirred for 1 hr at the same temperature and filtered to get a solid material. The obtained solid was washed with methanol to get 59 g (84%) of the title compound with >99% purity.

Example-6

Preparation of 1-(4-methoxy-phenyl)-7a-morpholin-4-yl-7-oxo-6-[4-(2-oxo-piperidin-1-yl)-phenyl-3a,4,5,6,7,7a-hexahydro-1H-pyrazolo[3,4-c]pyridine-3-carboxylic acid ethyl ester Method-A:
To a solution of ethyl acetate (2000 ml) and ethyl (2Z)-chloro[2-(4-methoxyphenyl) hydrazinylidene]ethanoate (250 g, 0.97 moles) was added to 340 g (0.97 moles) of 3-morpholin-4-yl-1-[4-(2-oxopiperidin-1-yl)phenyl]-5,6-dihydro-1H-pyridin-2-one under stirring at ambient temperature. The resulting reaction mass was cooled to 0-5° C. and 197 g (1.95 moles) of triethylamine were added. The reaction mass was heated to reflux and maintained at this temperature for 8-10 hrs. After completion, the reaction mass was cooled to ambient temperature, purified water (100 ml) was added and the layers were separated. The organic layer was distilled off completely under reduced pressure and the material was mixed with cyclohexane and isolated to obtain 450 g of the title compound (80%).

Method-B:
To a solution of ethyl (2Z)-chloro[2-(4-methoxyphenyl) hydrazinylidene]ethanoate (200 g 0.78 moles) in ethyl acetate (1000 ml) was added 278 g (0.78 moles) of 3-morpholin-4-yl-1-[4-(2-oxopiperidin-1-yl)phenyl]-5,6-dihydro-1H-pyridin-2-one under stirring at ambient temperature. The resulting reaction mass was cooled to 0-5° C. and 215 g (1.56 moles) of potassium carbonate were added. The reaction mass was heated to reflux and maintained for 10-12 hrs at this temperature. After completion, the reaction mass was cooled to ambient temperature, purified water (500 ml) was added and the layers were separated. The organic layer was distilled off completely under reduced pressure and the material was mixed with cyclohexane and isolated to obtain 390 g of the title compound (80.5%).

Method-C:
To a solution of ethyl (2Z)-chloro[2-(4-methoxyphenyl) hydrazinylidene]ethanoate (100 g, 0.39 moles) in ethyl acetate (1000 ml) was added 139 g (0.39 moles) of 3-morpholin-4-yl-1-[4-(2-oxopiperidin-1-yl)phenyl]-5,6-dihydro-1H-pyridin-2-one under stirring at ambient temperature. The resulting reaction mass was cooled to 0-5° C. and diisopropylethylamine (100 g, 0.78 moles) was added. The reaction mass was heated to reflux and maintained for 8-10 hrs at this temperature. After completion, the reaction mass was cooled to ambient temperature and purified water (500 ml) was added and the layers were separated. The organic layer was distilled off completely under reduced pressure and the material was mixed with cyclohexane and isolated to obtain 180 g of the title compound (75%).

Example-7

Preparation of 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester 1-(4-Methoxy-phenyl)-7a-morpholin-4-yl-7-oxo-6-[4-(2-oxo-piperidin-1-yl)-phenyl]-3a,4,5,6,7,7a-hexahydro-1H-pyrazolo[3,4-c]pyridine-3-carboxylic acid ethyl ester (450 g) was dissolved in isopropanol (1000 ml) and cooled to 0-5° C. Conc. HCl (500 ml) was added to the reaction mass under stirring and the reaction mixture was maintained for 4-5 hrs at to 0-5° C. After completion, methylene dichloride (2000 ml) and purified water (1000 ml) were charged to the reaction mass and stirred to separate layers. The organic layer was isolated, concentrated under reduced pressure and the isolated compound was treated with cyclohexane to obtain 400 g of the title compound (75%).

Example-8

Preparation of Apixaban

To a solution of 1-(4-methoxy-phenyl)-7-oxo-6-[4-(2-oxo-piperidin-1-yl)-phenyl]-4,5,6,7-tetrahydro-1H-Pyrzolo[3,4-c]pyridine-3-carboxylic acid ethyl ester (100 g) in N,N-dimethyl formamide (500 ml) was added formamide (92 g) under stirring at ambient temperature. The reaction mixture was cooled to 0-5° C., followed by addition of sodium methoxide solution (100 ml) at below 5° C. The reaction mass was stirred for 30 min at 0-5° C. and the temperature was raised to 25-30° C. and maintained for 3-4 hrs. After completion, the reaction mass was quenched with water (1000 ml) and stirred for 30 min. The resultant solid was filtered, washed with water (200 ml)/methyl tertiary butyl ether (200 ml) and dried at 40-50° C. for 10-12 hrs to obtain 75 g of the title compound (85%).

We claim:
1. A process for the preparation of Apixaban of formula (I),

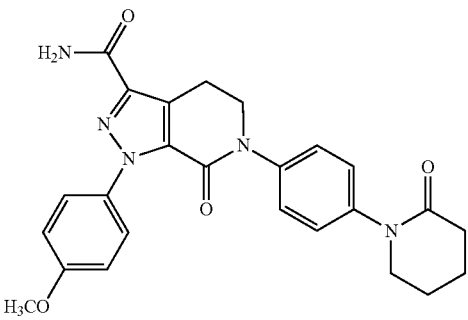

comprising the steps of:
a) condensing 1-(4-iodo-phenyl)-3-morpholin-4-yl-5,6-dihydro-1H-pyridin-2-one (VI) with δ-valerolactam in the presence of tripotassium phosphate ($K_3PO_4$)/Cu $(PPh_3)_3Br$ to produce 3-morpholin-4-yl-1-[4-(2-oxo-piperidin-1-yl)-phenyl]-5,6-dihydro-1H-pyridin-2-one (XIV),

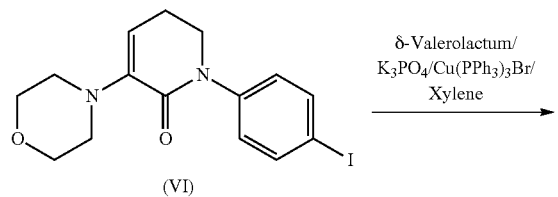

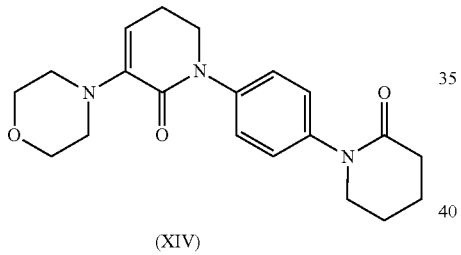

b) reacting the product of step-a) with ethyl (2Z)-chloro[2-(4-methoxyphenyl)hydrazinylidene]ethanoate (V) in a suitable solvent in the presence of triethyl amine ($Et_3N$) and further treated with hydrochloric acid to produce 1-(4-methoxy-phenyl)-7-oxo-6-[4-(2-oxo-piperidin-1-yl)-phenyl]-,4,5,6,7,tetrahydro-1H-pyrazolo[3,4-c]pyridine-3-carboxylic acid ethyl ester (II),

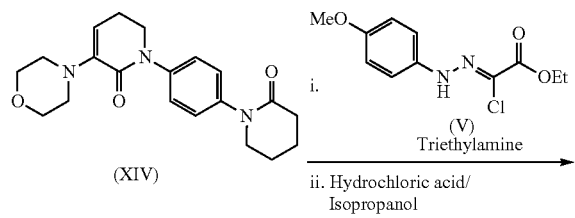

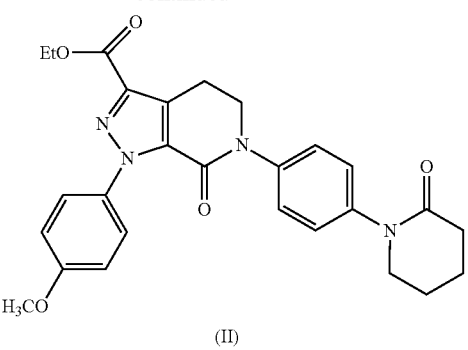

c) treating the product of step-b) with formamide, and

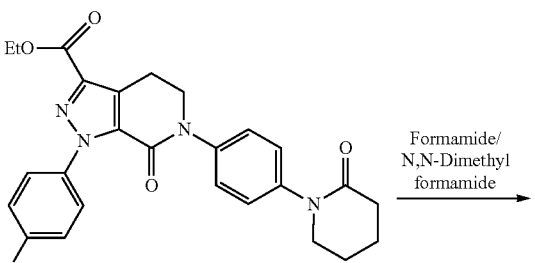

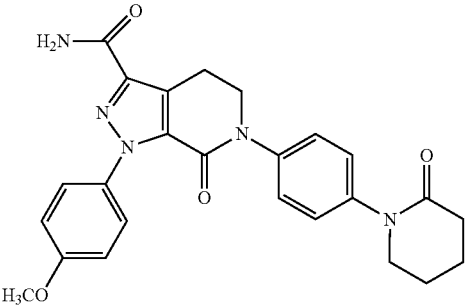

d) isolating Apixaban.

2. The process according to claim 1, wherein the suitable organic solvent used in step-b) is selected from the group consisting of methylene dichloride, chloroform, ethyl acetate, toluene, xylene, methanol, ethanol, isopropanol, dimethyl formamide, dimethyl sulfoxide, tetrahydrofuran, methyl ethyl ether and mixtures thereof.

* * * * *